(12) United States Patent
Shimatani et al.

(10) Patent No.: US 11,191,729 B2
(45) Date of Patent: Dec. 7, 2021

(54) GRANULAR MATERIAL FOR ORALLY FAST DISINTEGRATING TABLETS

(71) Applicant: Teika Pharmaceutical Co., Ltd., Toyama (JP)

(72) Inventors: Takao Shimatani, Toyama (JP); Yutaka Hasegawa, Toyama (JP); Hiroko Ito, Toyama (JP); Takahiro Kawagishi, Toyama (JP); Naohisa Wada, Toyama (JP); Atsushi Yamada, Toyama (JP)

(73) Assignee: Teika Pharmaceutical Co., Ltd., Toyama (JP)

( * ) Notice: Subject to any disclaimer, the term of this patent is extended or adjusted under 35 U.S.C. 154(b) by 373 days.

(21) Appl. No.: 16/077,991

(22) PCT Filed: Feb. 16, 2017

(86) PCT No.: PCT/JP2017/005619
§ 371 (c)(1),
(2) Date: Aug. 14, 2018

(87) PCT Pub. No.: WO2017/142001
PCT Pub. Date: Aug. 24, 2017

(65) Prior Publication Data
US 2020/0297641 A1    Sep. 24, 2020

(30) Foreign Application Priority Data
Feb. 16, 2016    (JP) .............................. JP2016-027029

(51) Int. Cl.
*A61K 9/20*    (2006.01)
*A61K 9/00*    (2006.01)

(52) U.S. Cl.
CPC .......... *A61K 9/2054* (2013.01); *A61K 9/0056* (2013.01); *A61K 9/2009* (2013.01); *A61K 9/2018* (2013.01); *A61K 9/2059* (2013.01); *A61K 9/2095* (2013.01)

(58) Field of Classification Search
None
See application file for complete search history.

(56) References Cited

U.S. PATENT DOCUMENTS

| 5,466,464 | A | 11/1995 | Masaki et al. |
| 2009/0118202 | A1* | 5/2009 | Thekkumkara ........... A61P 9/12 514/25 |
| 2010/0286286 | A1 | 11/2010 | Ikeda et al. |
| 2015/0238426 | A1 | 8/2015 | Shimatani et al. |

FOREIGN PATENT DOCUMENTS

| JP | 2807346 B2 | 10/1998 |
| JP | 2919771 B2 | 7/1999 |
| JP | 2000-119175 A | 4/2000 |
| JP | 2007-269789 A | 10/2007 |
| JP | 2014-224086 A | 12/2014 |
| JP | 2015-78166 A | 4/2015 |
| WO | WO 2009/066773 A1 | 5/2009 |
| WO | WO 2014/038593 A2 | 3/2014 |
| WO | WO 2015/115453 A1 | 8/2015 |

OTHER PUBLICATIONS

Machine translation, WO 2014/038593 (Year: 2014).*
International Preliminary Report on Patentability for PCT/JP2017/005619 dated Aug. 21, 2018.
International Search Report for PCT/JP2017/005619 dated Apr. 11, 2017.
Low-Substituted Hydroxypropyl Cellulose—Feb. 1, 2013, https://www.uspnf.com/errata/low-substituted-hydroxypropyl-cellulose-2013-02-01.
Hydroxypropyl Cellulose—Dec. 1, 2014, http://www.uspnf.com/errata/hydroxypropyl-cellulose-2014-12-01.
Hydroxypropyl cellulose and Low Substituted Hydroxypropyl Cellulose, Official Monographs, pp. 935-938.

* cited by examiner

*Primary Examiner* — Bethany P Barham
*Assistant Examiner* — Barbara S Frazier
(74) *Attorney, Agent, or Firm* — Knobbe, Martens, Olson & Bear, LLP

(57) ABSTRACT

The use of a granular material which is for orally fast disintegrating tablets and comprises starch and tannic acid allows provision of tablets that can be produced by a simple process with general-purpose production equipment, disintegrate fast and absorbs water in the mouth, and have a proper level of shape retainability for practical use. The present invention also provides a method for producing an orally fast disintegrating tablet, the method comprising compression molding of a granular material for orally fast disintegrating tablets comprising starch and tannic acid, or a mixture of the granular material for orally fast disintegrating tablets and other ingredients (an additive, an active ingredient, and/or the like).

13 Claims, No Drawings

GRANULAR MATERIAL FOR ORALLY FAST DISINTEGRATING TABLETS

CROSS REFERENCE TO RELATED APPLICATIONS

This application is a U.S. National Phase Application of PCT International Application Number PCT/JP2017/005619, filed on Feb. 16, 2017, designating the United States of America and published in the Japanese language, which is an International Application of and claims the benefit of priority to Japanese Patent Application No. 2016-027029, filed on Feb. 16, 2016. The disclosures of the above-referenced applications are hereby expressly incorporated by reference in their entireties.

TECHNICAL FIELD

The present invention relates to a granular material for orally fast disintegrating tablets which disintegrate fast and well in the presence of saliva or a small amount of water in the mouth; an orally fast disintegrating tablet containing the granular material; and a method for producing the orally fast disintegrating tablet.

BACKGROUND ART

Generally known dosage forms for oral solid preparations include tablets, capsules, granules and powders. However, these dosage forms are largely hard to handle and ingest. For example, tablets and capsules have a problem in that larger ones are harder to swallow, and granules and powders also have a problem in that they are easy to choke on and likely to get stuck between the teeth upon their ingestion. In addition, these dosage forms need to be taken with some water, and thus have difficulty in ingestion in the case of an emergency.

Known dosage forms that can be taken without water include chewable tablets, which are designed to be ingested by chewing. However, chewable tablets need sufficient chewing and swallowing abilities when taken, and are hard to take for elderly people, children, preschool children, patients with dysphagia, bedridden patients, and others.

Under such circumstances, there is a desire for the development of orally fast disintegrating tablets which can be easily taken without water and can be conveniently taken anytime and anywhere.

Known techniques for producing such orally fast disintegrating tablets include a method involving filling a mold (resin film sheet for PTP) with a suspension of an active ingredient and a saccharide in an aqueous agar solution, and solidifying the suspension into a jelly-like form, followed by reduced pressure drying or aeration drying (Patent Literature 1); and a method involving compressing tablet materials in a dry state containing a pharmaceutical agent, a water soluble binder and a water soluble excipient with a minimum pressure necessary for formation of tablets having a hardness enough to keep their shapes during the transition to the next step, wetting the resulting tablets, and drying the wet tablets (Patent Literature 2).

However, these methods are disadvantageous because they require special production equipment and thus are complicated as a production process.

Under such circumstances, there is a desire for the development of preparations that are producible by a simple process with general-purpose production equipment, excellent in oral disintegrability and water absorbability, and practically satisfactory in shape retainability.

CITATION LIST

Patent Literature

Patent Literature 1: Japanese Patent No. 2807346
Patent Literature 2: Japanese Patent No. 2919771

SUMMARY OF INVENTION

Technical Problem

Therefore, an object of the present invention is to provide an orally fast disintegrating tablet that can be produced by a simple process with general-purpose production equipment, disintegrates fast and absorbs water in the mouth, and has a proper level of shape retainability for practical use; a method for producing the orally fast disintegrating tablet; and a granular material used as an ingredient of the orally fast disintegrating tablet.

Solution to Problem

The present inventors have conducted extensive research to achieve the above-mentioned object, and as a result, have found that compression molding of a granular material comprising starch and tannic acid, or compression molding of this granular material with a binder and/or a disintegrant if needed, allows production of orally fast disintegrating tablets by a simple process with the use of not any special production equipment but general-purpose production equipment and that the resulting orally fast disintegrating tablets are equivalent or superior in disintegrability, water absorbability, and shape retainability to conventional orally fast disintegrating tablets.

The present invention has been completed based on the finding, and provides the following granular material for orally fast disintegrating tablets, the following orally fast disintegrating tablet, and the following method for producing an orally fast disintegrating tablet.
(1) A granular material for orally fast disintegrating tablets, the granular material comprising starch and tannic acid.
(2) The granular material for orally fast disintegrating tablets according to the above (1), wherein the content of starch is 0.001 to 60% by mass relative to the total mass of the granular material.
(3) The granular material for orally fast disintegrating tablets according to the above (1) or (2), wherein the starch is at least one kind selected from the group consisting of corn starch, potato starch, rice starch, wheat starch, sweet potato starch, mung bean starch, tapioca starch, partly pregelatinized starch, and pregelatinized starch.
(4) The granular material for orally fast disintegrating tablets according to any of the above (1) to (3), wherein the content of tannic acid is 0.001 to 60% by mass relative to the total mass of the granular material.
(5) The granular material for orally fast disintegrating tablets according to any of the above (1) to (4), further comprising an excipient.
(6) The granular material for orally fast disintegrating tablets according to the above (5), wherein the excipient is at least one kind selected from the group consisting of mannitol, erythritol, and lactose hydrate.
(7) An orally fast disintegrating tablet containing the granular material according to any of the above (1) to (6).

(8) The orally fast disintegrating tablet according to the above (7), further containing a binder and/or a disintegrant.
(9) The orally fast disintegrating tablet according to the above (8), wherein the binder is at least one kind selected from the group consisting of magnesium aluminometasilicate, synthetic aluminum silicate, light silicic acid anhydride, silicon dioxide, hydrated silicon dioxide, calcium silicate, and crystalline cellulose.
(10) The orally fast disintegrating tablet according to the above (8) or (9), wherein the disintegrant is at least one kind selected from the group consisting of crospovidone, croscarmellose sodium, carmellose calcium, carmellose, and low-substituted hydroxypropyl cellulose.
(11) The orally fast disintegrating tablet according to any of the above (7) to (10), having a disintegration time of 30 seconds or less as measured by a disintegration test.
(12) A method for producing an orally fast disintegrating tablet, comprising compression molding of (A) the granular material according to any of the above (1) to (6); (B) a mixture of the granular material according to any of the above (1) to (6) and an additive; or (C) a mixture of the granular material according to any of the above (1) to (6), an additive, and an active ingredient.
(13) The method according to the above (12), wherein the tableting pressure in the compression molding is 200 to 3000 kgf/cm$^2$.
(14) The method according to the above (12) or (13), wherein the additive is a binder and/or a disintegrant.

Advantageous Effects of Invention

The orally fast disintegrating tablet of the present invention exhibits an excellent disintegrability and water absorbability in the mouth as well as has a proper level of shape retainability, and thus is excellent in terms of the ease of ingestion.

That is, the orally fast disintegrating tablet of the present invention is excellent in disintegrability and water absorbability, and easily disintegrates in the mouth. Therefore, the tablet can be taken without water. In addition, although easily disintegrable tablets generally have lower hardness and are prone to breakage in the handling, the tablet of the present invention has a practically sufficient shape retainability, and therefore, does not require any special care of handling in the production, distribution, storage, ingestion, or the like.

DESCRIPTION OF EMBODIMENTS

Hereinafter, the present invention will be described in detail.
(I) Granular Material for Orally Fast Disintegrating Tablets The granular material of the present invention for orally fast disintegrating tablets is intended to be used for orally fast disintegrating tablets, and comprises starch and tannic acid.

In the present invention, "for orally fast disintegrating tablets" refers to having an application as a material for constituting or producing orally fast disintegrating tablets.
Starch The type of starch is not particularly limited as long as it is a natural starch usable in the formulations in the fields of pharmaceuticals, foods and the like, and examples of the starch include corn starch, potato starch, rice starch, wheat starch, sweet potato starch, mung bean starch, tapioca starch, partly pregelatinized starch, and pregelatinized starch. Preferred are corn starch, wheat starch, rice starch, and potato starch. The starch used may be of one kind or any combination of two or more kinds.

The amount of starch in the granular material is preferably about 0.001% by mass or more, more preferably about 0.01% by mass or more, and still more preferably about 0.1% by mass or more relative to the total mass of the granular material. When the amount of starch is as above, tablets produced from the granular material of the present invention have sufficient disintegrability and water absorbability. In addition, the amount of starch is preferably 60% by mass or less, more preferably about 30% by mass or less, and still more preferably about 10% by mass or less. When the amount of starch is as above, tablets produced from the granular material of the present invention have sufficient shape retainability.
Tannic Acid The type of tannic acid is not particularly limited as long as it is usable in the formulations in the fields of pharmaceuticals, foods and the like, and such a tannic acid can be extracted with water or ethanol from various plant materials including persimmon fruit, chestnut astringent skin, *Rhus chinensis* galls (*Galla chinensis*), *Quercus infectoria* galls, Tara powder, tamarind (family Fabaceae) seed coat, mimosa bark, etc. In particular, preferred is tannic acid extracted from *Rhus chinensis* galls or *Quercus infectoria* galls as specified in the Japanese Pharmacopoeia, 16th edition. The tannic acid used may be in an unpurified or purified state, but is preferably in a purified state.

The amount of tannic acid in the granular material is preferably about 0.001% by mass or more, more preferably about 0.01% by mass or more, and still more preferably about 0.1% by mass or more relative to the total mass of the granular material. When the amount of tannic acid is as above, tablets produced from the granular material of the present invention have sufficient disintegrability and water absorbability. In addition, the amount of tannic acid is preferably 60% by mass or less, more preferably about 30% by mass or less, and still more preferably about 10% by mass or less. When the amount of tannic acid is as above, tablets produced from the granular material of the present invention have sufficient shape retainability.
The Ratio of Starch and Tannic Acid The mass ratio of starch and tannic acid (starch:tannic acid) in the granular material is preferably about 1:10 to 0.01, more preferably about 1:5 to 0.02, and still more preferably about 1:2 to 0.05. When the ratio is as above, tablets produced from the granular material of the present invention have disintegrability and water absorbability as well as shape retainability.
Other Ingredients The granular material desirably comprises, in addition to the above-described starch and tannic acid, an excipient. Tablets produced from such a granular material have further improved shape retainability, disintegrability, and water absorbability.

Examples of the excipient include sugar alcohols such as mannitol, sorbitol, xylitol, erythritol, maltitol and isomalt; saccharides such as lactose hydrate, anhydrous lactose, sucrose, purified sucrose, fructose, glucose, glucose hydrate and trehalose; amino acids such as glycine and alanine; silicic acid compounds such as light silicic acid anhydride, silicon dioxide, hydrated silicon dioxide, synthetic aluminum silicate, magnesium aluminometasilicate, and calcium silicate; and cellulosic compounds such as crystalline cellulose and powdered cellulose. For easy disintegration of the granular material in saliva in the mouth, preferred are sugar alcohols and saccharides, and among them, particularly preferred are mannitol, erythritol, and lactose hydrate.

The excipient used may be of one kind or any combination of two or more kinds.

The granular material can further comprise an appropriate amount of another additive commonly used in food or pharmaceutical products, such as a lubricant, a colorant, a corrigent, a sweetener, a flavoring agent, and a preservative.

Examples of the lubricant include magnesium stearate, calcium stearate, talc, sucrose fatty acid ester, and sodium stearyl fumarate.

Examples of the colorant include food dyes, food lake dyes, red ferric oxide, and yellow ferric oxide.

Examples of the corrigent include citric acid hydrate, anhydrous citric acid, tartaric acid, malic acid, and ascorbic acid.

Examples of the sweetener include aspartame, acesulfame potassium, saccharin, sodium saccharin, dipotassium glycyrrhizinate, stevia, thaumatin, and sucralose.

Examples of the flavoring agent include fennel oil, orange oil, German chamomile oil, spearmint oil, cinnamon oil, clove oil, mentha oil, bergamot oil, eucalyptus oil, lavender oil, lemon oil, rose oil, Roman chamomile oil, and menthol.

Examples of the preservative include benzoic acid, sodium benzoate, benzyl benzoate, isobutyl p-hydroxybenzoate, isopropyl p-hydroxybenzoate, ethyl p-hydroxybenzoate, butyl p-hydroxybenzoate, propyl p-hydroxybenzoate, propyl p-hydroxybenzoate sodium salt, methyl p-hydroxybenzoate, and methyl p-hydroxybenzoate sodium salt.

The additive used may be of one kind or any combination of two or more kinds.

The granular material can comprise an appropriate amount of an active ingredient for a food or pharmaceutical product. The type and the amount of each active ingredient are not particularly limited as long as the type and amount do not impair the moldability, disintegrability, or water absorbability of the granular material. Examples of the active ingredient include an antioxidant, such as tetrahydro curcumin; an antiallergic drug, such as ketotifen fumarate; an antidiarrheal drug, such as loperamide hydrochloride; etc.

Granulation

The granulation process to prepare a granular material comprising the above-described ingredients may be either a wet granulation process or a dry granulation process. For convenience, preferred is a wet granulation process, in particular, an agitation granulation process or a fluid bed granulation process.

The agitation granulation process involves kneading all the ingredients with a solvent and then granulating the resulting wet mass. This process can utilize the protocol and equipment used in agitation granulation etc. for the production of ordinary preparations. The fluid bed granulation process involves spraying a solvent alone or a solvent mixed with a binder etc. to the ingredients for granular formation. This process can utilize the protocol and equipment used in fluid bed granulation etc. for the production of ordinary preparations. The solvent that can be used in the above-mentioned processes is a solvent used for the production of ordinary preparations, such as alcohols such as ethanol and isopropanol, and water.

The dry granulation process involves uniformly mixing all the ingredients and then granulating the mixture. This process can utilize the protocol and equipment used in compression granulation etc. for the production of ordinary preparations.

(II) Orally Fast Disintegrating Tablet

For production of the orally fast disintegrating tablet of the present invention (hereinafter also called "the tablet of the present invention") from the above-described granular material, the granular material of the present invention is mixed with other ingredients such as a binder and a disintegrant as appropriate, and the mixture is then subjected to compression molding. The compression molding can utilize the protocol and equipment used for the molding of ordinary tablets in a rotary tablet press, a single punch tablet press, etc.

The compression pressure in the compression molding is preferably about 200 kgf/cm$^2$ (about 2 kN) or more, more preferably about 400 kgf/cm$^2$ (about 4 kN) or more, and still more preferably about 600 kgf/cm$^2$ (about 6 kN) or more. In addition, the compression pressure is preferably about 3000 kgf/cm$^2$ (about 30 kN) or less, more preferably about 2000 kgf/cm$^2$ (about 20 kN) or less, and still more preferably about 1000 kgf/cm$^2$ (about 10 kN) or less. When the compression pressure is in the above range, the load imposed on the dies and punches during the tableting operation is modest and the tableting pressure is easy to keep constant during the tableting operation.

The compression molding of the granular material may be preceded by other procedures required for tablet production, for example, drying with a fluid bed dryer, a shelf dryer or the like; particle size adjustment with a screen mill, a jet mill, a hammer mill, a pin mill or the like; sieving with a vibrating sieve; etc.

The tablet of the present invention can substantially be composed of only the above-described granular material of the present invention, but an additional ingredient such as a binder and a disintegrant can also be contained in the tablet.

When the tablet of the present invention contains other ingredients in addition to the granular material of the present invention, the amount of the granular material in the tablet of the present invention is preferably about 10% by mass or more, more preferably about 30% by mass or more, and still more preferably about 60% by mass or more relative to the total mass of the tablet. That is, the amount of the other ingredients is preferably about 90% by mass or less, more preferably about 70% by mass or less, and still more preferably about 40% by mass or less relative to the total mass of the tablet. When the amount of the other ingredients is in the above range, a practically sufficient level of shape retainability, disintegrability, and water absorbability can be achieved.

Since the tablet of the present invention is produced by compression molding, the shape of the granular material present in the tablet is usually different from the original shape of the granular material.

Binder

The tablet of the present invention can contain a binder. Binders serve to combine granular materials together under compression.

Examples of the binder include magnesium aluminometasilicate, synthetic aluminum silicate, light silicic acid anhydride, silicon dioxide, hydrated silicon dioxide, calcium silicate, crystalline cellulose, powdered cellulose, low-substituted hydroxypropyl cellulose, povidone, hydroxypropyl cellulose, hypromellose phthalate, hydroxypropylmethylcellulose acetate succinate, carmellose sodium, ethyl cellulose, methyl cellulose, hypromellose, gum arabic, sodium alginate, dextrin, corn starch, potato starch, wheat starch, rice starch, partly pregelatinized starch, pregelatinized starch, gelatin, pullulan, carboxyvinyl polymer, etc. In particular, magnesium aluminometasilicate, synthetic aluminum silicate, light silicic acid anhydride, silicon dioxide, hydrated silicon dioxide, calcium silicate, and crystalline cellulose are preferable.

The binder used may be of one kind or any combination of two or more kinds.

The amount of the binder is preferably about 0.01% by mass or more, more preferably about 0.1% by mass or more, and still more preferably about 1% by mass or more relative to the total mass of the tablet.

In addition, the amount of the binder is preferably about 30% by mass or less, more preferably about 20% by mass or less, and still more preferably about 10% by mass or less relative to the total mass of the tablet. When the amount of the binder is in the above range, a practically sufficient level of binder function is provided, and the resulting tablet has a sufficient level of shape retainability, disintegrability, and water absorbability.

Disintegrant

The tablet of the present invention can contain a disintegrant. Disintegrants are ingredients which absorb water and subsequently swell, or ingredients which absorb water and thereby facilitate the breakup of the composition.

Examples of the disintegrant include crospovidone, carmellose calcium, carmellose, alginic acid, croscarmellose sodium, low-substituted hydroxypropyl cellulose, corn starch, potato starch, wheat starch, rice starch, partially pregelatinized starch, pregelatinized starch and sodium carboxymethyl starch. In particular, crospovidone, croscarmellose sodium, carmellose calcium, carmellose, and low-substituted hydroxypropyl cellulose are preferable.

The disintegrant used may be of one kind or any combination of two or more kinds.

The amount of the disintegrant is preferably about 0.01% by mass or more, more preferably about 0.1% by mass or more, and still more preferably about 1% by mass or more relative to the total mass of the tablet.

In addition, the amount of the disintegrant is preferably about 30% by mass or less, more preferably about 20% by mass or less, and still more preferably about 10% by mass or less relative to the total mass of the tablet. When the amount of the disintegrant is in the above range, a practically sufficient level of disintegrant function is provided, and the resulting tablet has a sufficient level of shape retainability, disintegrability, and water absorbability.

Other Ingredients

The tablet of the present invention can further contain an appropriate amount of another additive commonly used in a food or pharmaceutical product, such as an excipient, a lubricant, a colorant, a corrigent, a sweetener, a flavoring agent, and a preservative. The additive used may be of one kind or any combination of two or more kinds.

The tablet of the present invention can comprise one or more kinds of active ingredients in addition to the granular material. Examples of the active ingredient include an antioxidant, such as tetrahydro curcumin; an antiallergic drug, such as ketotifen fumarate; an antidiarrheal drug, such as loperamide hydrochloride; etc.

The thus obtained tablets of the present invention have a proper level of shape retainability for practical use, and also are excellent in oral disintegrability and water absorbability.

The disintegration time and water absorption time of the tablet of the present invention is preferably 60 seconds or less, more preferably 45 seconds or less, and still more preferably 30 seconds or less. Furthermore, the hardness of the tablet of the present invention is preferably 30 N or more, more preferably 40 N or more, and still more preferably 50 N or more.

The disintegration time, water absorption time, and hardness are each measured by the method described in EXAMPLES.

EXAMPLES

Hereinafter, the present invention will be illustrated in more detail by examples and comparative examples, but is not limited to these examples.

(1) Physical Property Testing

Disintegration Test

The disintegration time was measured for 6 tablets per sample based on the disintegration test specified in the manual of the Japanese Pharmacopoeia, 16th edition using a disintegration tester (manufactured by Toyama Sangyo Co., Ltd.).

Water Absorbability Test

The water absorption time was measured for 3 tablets per sample in the following manner. Into a petri dish 6.5 cm in diameter, 6 mL of water was poured, and a piece of water-insoluble tissue paper folded into four was placed in the petri dish. After the tissue paper became completely wet, a tablet was placed thereon, and the time required for the entire tablet to become wet was measured.

Hardness Test

The test was performed for 10 tablets per sample using a load cell type tablet hardness tester (manufactured by Okada Seiko Co., Ltd.).

(2) Tablet Production

Examples 1

Based on the composition shown in Table 1 below, tetrahydro curcumin, lactose hydrate, corn starch, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Example 2

Based on the composition shown in Table 1 below, tetrahydro curcumin, lactose hydrate, corn starch, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Example 3

Based on the composition shown in Table 1 below, tetrahydro curcumin, lactose hydrate, corn starch, and crystalline cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Comparative Example 1

Based on the composition shown in Table 1 below, tetrahydro curcumin, lactose hydrate, corn starch, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Comparative Example 2

Based on the composition shown in Table 1 below, tetrahydro curcumin, lactose hydrate, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Example 4

Based on the composition shown in Table 2 below, lactose hydrate, corn starch, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Comparative Example 3

Based on the composition shown in Table 2 below, lactose hydrate, corn starch, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Comparative Example 4

Based on the composition shown in Table 2 below, lactose hydrate, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Comparative Example 5

Based on the composition shown in Table 2 below, lactose hydrate, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Example 5

Based on the composition shown in Table 3 below, tetrahydro curcumin, lactose hydrate, corn starch, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tableting pressure of about 800 kgf/cm$^2$ (about 8 kN) into tablets each having a diameter of 8 mm and a mass of 220 mg.

Comparative Example 6

Based on the composition shown in Table 3 below, tetrahydro curcumin, lactose hydrate, corn starch, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 7

Based on the composition shown in Table 3 below, tetrahydro curcumin, lactose hydrate, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 8

Based on the composition shown in Table 3 below, tetrahydro curcumin, lactose hydrate, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Example 6

Based on the composition shown in Table 4 below, ketotifen fumarate, lactose hydrate, corn starch, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 9

Based on the composition shown in Table 4 below, ketotifen fumarate, lactose hydrate, corn starch, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 10

Based on the composition shown in Table 4 below, ketotifen fumarate, lactose hydrate, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 11

Based on the composition shown in Table 4 below, ketotifen fumarate, lactose hydrate, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Example 7

Based on the composition shown in Table 5 below, loperamide hydrochloride, lactose hydrate, corn starch, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 12

Based on the composition shown in Table 5 below, loperamide hydrochloride, lactose hydrate, corn starch, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 13

Based on the composition shown in Table 5 below, loperamide hydrochloride, lactose hydrate, crystalline cellulose, and hydroxypropyl cellulose were mixed in a mixing granulator, and to this, a solution of tannic acid and sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

Comparative Example 14

Based on the composition shown in Table 5 below, loperamide hydrochloride, lactose hydrate, crystalline cellulose, and hydroxypropyl cellulose were mixed in a mixing granulator, and to this, a solution of sucralose in an appropriate amount of dehydrated ethanol/water (1:1) mixture as a granulation solvent was gradually added to give granules. Next, the granules were dried in a shelf dryer, and the dried granules were subjected to particle size adjustment. To the uniformly sized granules, the other additives were added, and the whole was mixed and fed into a rotary tablet press, in which the mixture was then compressed at a tabletting pressure of about 800 kgf/cm$^2$ (about 8 kN) into tablets each having a diameter of 8 mm and a mass of 220 mg.

(3) Results

The compositions of the tablets of Examples 1 to 3 and Comparative Examples 1 and 2, and their measurement results for hardness, disintegration time, and water absorption time are shown in the following Table 1.

TABLE 1

| Ingredient | Unit: g | | | | |
|---|---|---|---|---|---|
| | Example 1 | Example 2 | Example 3 | Comparative Example 1 | Comparative Example 2 |
| Tetrahydro curcumin | 300 | 300 | 300 | 300 | 300 |
| Lactose hydrate | 1160 | 1360 | 1220 | 1200 | 1460 |
| Corn starch | 300 | 300 | 300 | 300 | — |
| Crystalline cellulose | 200 | — | 200 | 200 | 200 |
| Hydroxypropyl cellulose | 60 | 60 | — | 60 | 60 |
| Tannic acid | 40 | 40 | 40 | — | 40 |
| Sucralose | 1.2 | 1.2 | 1.2 | 1.2 | 1.2 |
| Carmellose calcium | 44 | 44 | 44 | 44 | 44 |
| Silicon dioxide | 44 | 44 | 44 | 44 | 44 |
| Aspartame | 10.8 | 10.8 | 10.8 | 10.8 | 10.8 |
| Anhydrous citric acid | 19 | 19 | 19 | 19 | 19 |
| Flavoring agent | 6 | 6 | 6 | 6 | 6 |
| Calcium stearate | 15 | 15 | 15 | 15 | 15 |
| Total | 2200 | 2200 | 2200 | 2200 | 2200 |
| Hardness (N) | 64 | 62 | 54 | 64 | 89 |
| Disintegration time (sec) | 15 | 18 | 25 | 38 | 320 |
| Absorption time (sec) | 35 | 38 | 31 | 417 | 138 |

As clearly shown in Table 1, the tablets of Example 1, Example 2, and Example 3 had a hardness of not less than 50 N, and both a disintegration time and a water absorption time of not more than 60 seconds, and were excellent in shape retainability, disintegrability, and water absorbability, regardless of the presence or absence of crystalline cellulose and hydroxypropyl cellulose.

In contrast, regarding the tablet of Comparative Example 1, which did not contain tannic acid, the hardness was not less than 50 N and the disintegration time was not more than 60 seconds, meaning a practically acceptable shape retainability and disintegrability, but the water absorption time was 417 seconds, exceeding 60 seconds and meaning a significantly poor water absorbability. Regarding the tablet of Comparative Example 2, which did not contain corn starch, the hardness was not less than 50 N, meaning a practically acceptable shape retainability, but the disintegration time was 320 seconds and the water absorption time was 138 seconds, both exceeding 60 seconds and meaning a significantly poor disintegrability and water absorbability.

The compositions of the tablets of Example 4 and Comparative Examples 3 to 5, and their measurement results for hardness, disintegration time and water absorption time are shown in the following Table 2.

TABLE 2

| Ingredient | Unit: g | | | |
|---|---|---|---|---|
| | Example 4 | Comparative Example 3 | Comparative Example 4 | Comparative Example 5 |
| Lactose hydrate | 1466 | 1506 | 1766 | 1806 |
| Corn starch | 300 | 300 | — | — |
| Crystalline cellulose | 200 | 200 | 200 | 200 |
| Hydroxypropyl cellulose | 60 | 60 | 60 | 60 |
| Tannic acid | 40 | — | 40- | — |
| Sucralose | 1.2 | 1.2 | 1.2 | 1.2 |
| Carmellose calcium | 44 | 44 | 44 | 44 |
| Silicon dioxide | 44 | 44 | 44 | 44 |
| Aspartame | 10.8 | 10.8 | 10.8 | 10.8 |
| Anhydrous citric acid | 19 | 19 | 19 | 19 |
| Calcium stearate | 15 | 15 | 15 | 15 |
| Total | 2200 | 2200 | 2200 | 2200 |
| Hardness (N) | 78 | 67 | 90 | 79 |
| Disintegration time (sec) | 34 | 82 | 40 | 73 |
| Absorption time (sec) | 55 | 302 | 76 | 19 min |

As clearly shown in Table 2, the tablet of Example 4 had both a disintegration time and a water absorption time of not more than 60 seconds and a hardness of not less than 50 N, and were excellent in disintegrability, water absorbability, and shape retainability. In contrast, regarding the tablets of Comparative Examples 3 to 5, the hardness was not less than 50 N, meaning an excellent shape retainability, but the disintegrability and the water absorbability were significantly poor as compared with Example 4. Specifically, the tablet of Comparative Example 3, which did not contain tannic acid, had a disintegration time of 82 seconds and a water absorption time of 302 seconds, the tablet of Comparative Example 4, which did not contain corn starch, had a disintegration time of 40 seconds and a water absorption time of 76 seconds, and the tablet of Comparative Example 5, which did contain neither tannic acid nor corn starch, had a disintegration time of 73 seconds and a water absorption time of 19 minutes.

The compositions of the tablets of Example 5 and Comparative Examples 6 to 8, and their measurement results for hardness, disintegration time and water absorption time are shown in the following Table 3.

TABLE 3

| Ingredient | Example 5 | Comparative Example 6 | Comparative Example 7 | Comparative Example 8 |
|---|---|---|---|---|
| Tetrahydro curcumin | 300 | 300 | 300 | 300 |
| Lactose hydrate | 1166 | 1206 | 1466 | 1506 |
| Corn starch | 300 | 300 | — | — |
| Crystalline cellulose | 200 | 200 | 200 | 200 |
| Hydroxypropyl cellulose | 60 | 60 | 60 | 60 |
| Tannic acid | 40 | — | 40- | — |
| Sucralose | 1.2 | 1.2 | 1.2 | 1.2 |
| Carmellose calcium | 44 | 44 | 44 | 44 |
| Silicon dioxide | 44 | 44 | 44 | 44 |
| Aspartame | 10.8 | 10.8 | 10.8 | 10.8 |
| Anhydrous citric acid | 19 | 19 | 19 | 19 |
| Calcium stearate | 15 | 15 | 15 | 15 |
| Total | 2200 | 2200 | 2200 | 2200 |
| Hardness (N) | 75 | 78 | 92 | 99 |
| Disintegration time (sec) | 21 | 41 | 234 | 70 |
| Absorption time (sec) | 39 | 456 | 119 | 49 min |

As clearly shown in Table 3, the tablet of Example 5 had both a disintegration time and a water absorption time of not more than 60 seconds and a hardness of not less than 50 N, and were excellent in disintegrability, water absorbability, and shape retainability. In contrast, regarding the tablets of Comparative Examples 6 to 8, the hardness was not less than 50 N, meaning an excellent shape retainability, but the disintegrability and the water absorbability were significantly poor as compared with Example 5. Specifically, the tablet of Comparative Example 6, which did not contain tannic acid, had a disintegration time of 41 seconds and a water absorption time of 456 seconds, the tablet of Comparative Example 7, which did not contain corn starch, had a disintegration time of 234 seconds and a water absorption time of 119 seconds, and the tablet of Comparative Example 8, which did contain neither tannic acid nor corn starch, had a disintegration time of 70 seconds and a water absorption time of 49 minutes.

The compositions of the tablets of Example 6 and Comparative Examples 9 to 11, and their measurement results for hardness, disintegration time and water absorption time are shown in the following Table 4.

TABLE 4

| Ingredient | Example 6 | Comparative Example 9 | Comparative Example 10 | Comparative Example 11 |
|---|---|---|---|---|
| Ketotifen funnarate | 13.8 | 13.8 | 13.8 | 13.8 |
| Lactose hydrate | 1452.2 | 1492.2 | 1752.2 | 1792.2 |
| Corn starch | 300 | 300 | — | — |
| Crystalline cellulose | 200 | 200 | 200 | 200 |
| Hydroxypropyl cellulose | 60 | 60 | 60 | 60 |
| Tannic acid | 40 | — | 40- | — |
| Sucralose | 1.2 | 1.2 | 1.2 | 1.2 |
| Carmellose calcium | 44 | 44 | 44 | 44 |
| Silicon dioxide | 44 | 44 | 44 | 44 |
| Aspartame | 10.8 | 10.8 | 10.8 | 10.8 |
| Anhydrous citric acid | 19 | 19 | 19 | 19 |
| Calcium stearate | 15 | 15 | 15 | 15 |
| Total | 2200 | 2200 | 2200 | 2200 |
| Hardness (N) | 61 | 60 | 72 | 78 |
| Disintegration time (sec) | 19 | 91 | 46 | 111 |
| Absorption time (sec) | 35 | 229 | 77 | 36 min |

As clearly shown in Table 4, the tablet of Example 6 had both a disintegration time and a water absorption time of not more than 60 seconds and a hardness of not less than 50 N, and were excellent in disintegrability, water absorbability, and shape retainability. In contrast, regarding the tablets of Comparative Examples 9 to 11, the hardness was not less than 50 N, meaning an excellent shape retainability, but the disintegrability and the water absorbability were significantly poor as compared with Example 6. Specifically, the tablet of Comparative Example 9, which did not contain tannic acid, had a disintegration time of 91 seconds and a water absorption time of 229 seconds, the tablet of Comparative Example 10, which did not contain corn starch, had a disintegration time of 46 seconds and a water absorption time of 77 seconds, and the tablet of Comparative Example 11, which did contain neither tannic acid nor corn starch, had a disintegration time of 111 seconds and a water absorption time of 36 minutes.

The compositions of the tablets of Example 7 and Comparative Examples 12 to 14, and their measurement results for hardness, disintegration time and water absorption time are shown in the following Table 5.

TABLE 5

| Ingredient | Example 7 | Comparative Example 12 | Comparative Example 13 | Comparative Example 14 |
|---|---|---|---|---|
| Loperamide hydrochloride | 5 | 5 | 5 | 5 |
| Lactose hydrate | 1461 | 1501 | 1761 | 1801 |
| Corn starch | 300 | 300 | — | — |
| Crystalline cellulose | 200 | 200 | 200 | 200 |
| Hydroxypropyl cellulose | 60 | 60 | 60 | 60 |
| Tannic acid | 40 | — | 40- | — |
| Sucralose | 1.2 | 1.2 | 1.2 | 1.2 |
| Carmellose calcium | 44 | 44 | 44 | 44 |
| Silicon dioxide | 44 | 44 | 44 | 44 |
| Aspartame | 10.8 | 10.8 | 10.8 | 10.8 |
| Anhydrous citric acid | 19 | 19 | 19 | 19 |

TABLE 5-continued

| | Unit: g | | | |
|---|---|---|---|---|
| Ingredient | Example 7 | Comparative Example 12 | Comparative Example 13 | Comparative Example 14 |
| Calcium stearate | 15 | 15 | 15 | 15 |
| Total | 2200 | 2200 | 2200 | 2200 |
| Hardness (N) | 72 | 61 | 78 | 82 |
| Disintegration time (sec) | 19 | 79 | 36 | 71 |
| Absorption time (sec) | 46 | 272 | 95 | 22 min |

As clearly shown in Table 5, the tablet of Example 7 had both a disintegration time and a water absorption time of not more than 60 seconds and a hardness of not less than 50 N, and were excellent in disintegrability, water absorbability, and shape retainability. In contrast, regarding the tablets of Comparative Examples 12 to 14, the hardness was not less than 50 N, meaning an excellent shape retainability, but the disintegrability and the water absorbability were significantly poor as compared with Example 7. Specifically, the tablet of Comparative Example 12, which did not contain tannic acid, had a disintegration time of 79 seconds and a water absorption time of 272 seconds, the tablet of Comparative Example 13, which did not contain corn starch, had a disintegration time of 36 seconds and a water absorption time of 95 seconds, and the tablet of Comparative Example 14, which did contain neither tannic acid nor corn starch, had a disintegration time of 71 seconds and a water absorption time of 22 minutes.

INDUSTRIAL APPLICABILITY

The orally fast disintegrating tablet of the present invention can be produced without the use of any complicated production process or any special production equipment, and is excellent in functions, such as shape retainability, disintegrability, and water absorbability. Therefore, the tablet of the present invention can be widely used as an orally fast disintegrating tablet that is suitable for industrial mass production and can contain a variety of pharmaceutically active ingredients.

The invention claimed is:

1. A tablet comprising a granular material, which comprises corn starch, tannic acid, and a disintegrant, wherein the disintegrant is carmellose calcium and the tablet is configured such that it has a water absorption time of not more than 60 seconds.

2. The tablet according to claim 1, wherein the content of starch is 0.001 to 60% by mass relative to the total mass of the granular material.

3. The tablet according to claim 1, wherein the content of tannic acid is 0.001 to 60% by mass relative to the total mass of the granular material.

4. The tablet according to claim 1, further comprising an excipient.

5. The tablet according to claim 4, wherein the excipient is selected from the group consisting of mannitol, erythritol, and lactose hydrate.

6. The tablet according to claim 1, further comprising a binder.

7. The tablet according to claim 6, wherein the binder is selected from the group consisting of magnesium aluminometasilicate, synthetic aluminum silicate, light silicic acid anhydride, silicon dioxide, hydrated silicon dioxide, calcium silicate, and crystalline cellulose.

8. The tablet according to claim 6, wherein said tablet is configured to have a disintegration time of 30 seconds or less as measured by a disintegration test.

9. The tablet according to claim 1, wherein the tablet is configured such that it has a hardness of not less than 50 N and a disintegration time of not more than 60 seconds.

10. A method for producing the tablet of claim 1, comprising compression molding of: (A) a granular material comprising corn starch, tannic acid, and a disintegrant, wherein the disintegrant is carmellose calcium; (B) a mixture of said granular material and an additive; or (C) a mixture of said granular material, an additive, and an active ingredient.

11. The method according to claim 10, wherein the tableting pressure in the compression molding is 200 to 3000 kgf/cm$^2$.

12. The method according to claim 10, wherein the additive is a binder.

13. The method according to claim 10, wherein the tablet is configured such that it has a hardness of not less than 50 N and a water absorption time of not more than 60 seconds.

* * * * *